United States Patent [19]
Kikuchi et al.

[11] Patent Number: 5,242,917
[45] Date of Patent: Sep. 7, 1993

[54] TETRACARBOXYLIC ACID DIANHYDRIDE HAVING DISILOXANE LINKAGE AND PROCESS FOR PRODUCING THE SAME

[75] Inventors: Tohru Kikuchi; Koichi Kamijima; Takayuki Saito, all of Hitachi, Japan

[73] Assignee: Hitachi Chemical Company, Ltd., Tokyo, Japan

[21] Appl. No.: 668,170

[22] Filed: Mar. 13, 1991

Related U.S. Application Data

[63] Continuation of Ser. No. 277,966, Nov. 30, 1988, abandoned.

[30] Foreign Application Priority Data

Dec. 10, 1987 [JP] Japan ................. 62-313051

[51] Int. Cl.$^5$ ................................................ C07F 7/07
[52] U.S. Cl. ........................................ 514/214; 528/27
[58] Field of Search ........................... 549/214; 528/27

[56] References Cited

FOREIGN PATENT DOCUMENTS 0292260 5/1988 European Pat. Off. .

OTHER PUBLICATIONS

K. L. Mittal, "Polyimides," vol. 1, pp. 51-64, Plenum Press, New York, (1984).
R. T. Morrison and R. N. Boyd, "Organic Chemistry," 3rd ed., pp. 374-375, Allyn and Bacon, Inc., Boston (1973).
J. R. Pratt, et al., *J. Org. Chem.*, "Organosilicon Compounds," 38(25), pp. 4271-4274 (1973).

*Primary Examiner*—Mark Russell
*Attorney, Agent, or Firm*—Antonelli, Terry, Stout & Kraus

[57] ABSTRACT

1-(2,3-Dicarboxyphenyl)-3-(3,4-dicarboxyphenyl)-1,1,3,3-tetramethyldisiloxane dianhydride is useful as a curing agent for epoxy resins.

6 Claims, 3 Drawing Sheets

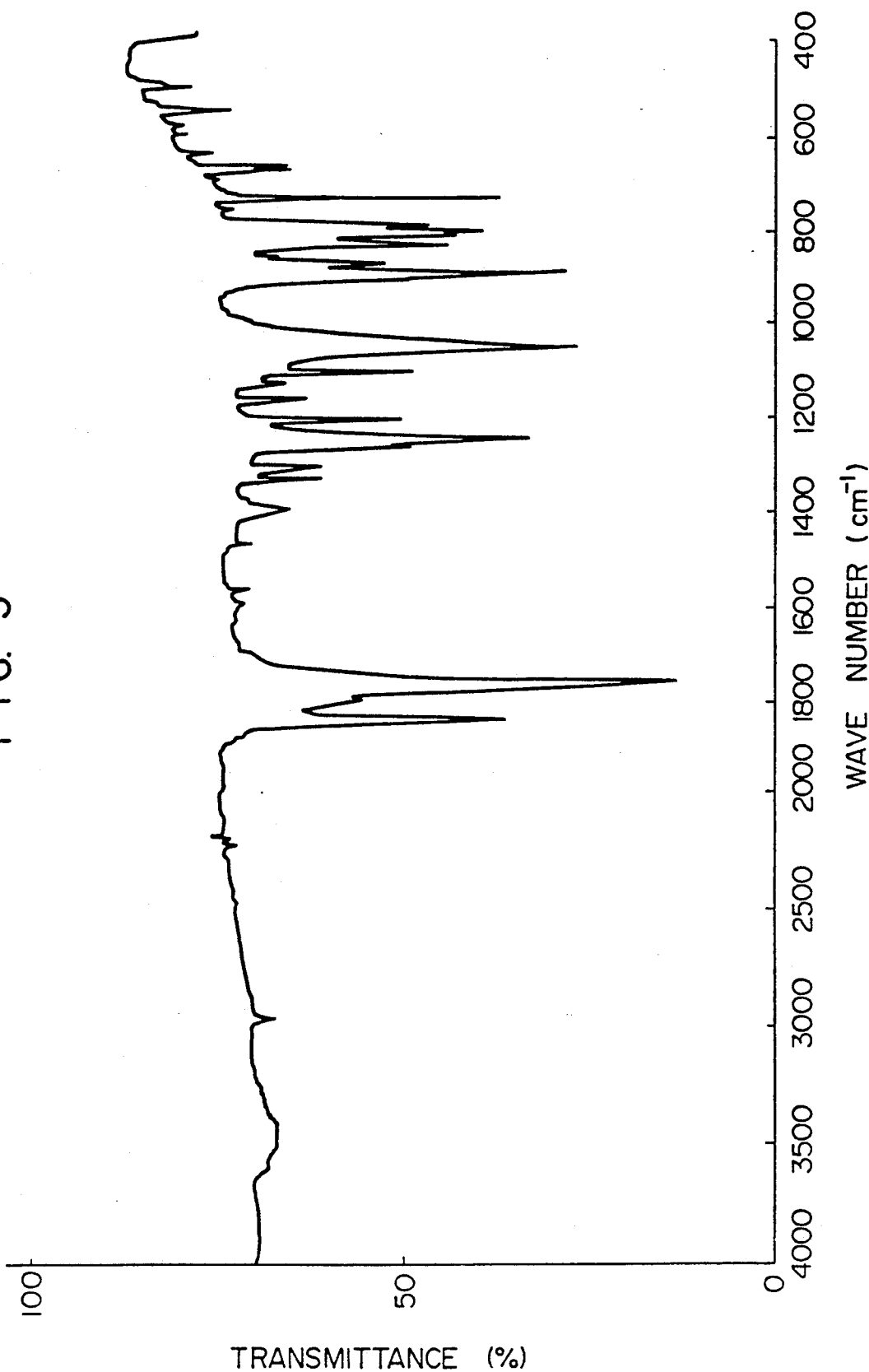

TETRACARBOXYLIC ACID DIANHYDRIDE HAVING DISILOXANE LINKAGE AND PROCESS FOR PRODUCING THE SAME

This is a continuation of application Ser. No. 277,966, filed Nov. 30, 1988 now abandoned.

BACKGROUND OF THE INVENTION

This invention relates to a tetracarboxylic acid dianhydride having a disiloxane linkage and useful as an epoxy resin curing agent, more particularly to 1-(2,3-dicarboxyphenyl)-3-(3,4-dicarboxyphenyl)-1, 1,3,3-tetramethyldisiloxane dianhydride and a process for producing the same.

1,3-Bis(3,4-dicarboxyphenyl)-1,1,3,3-tetramethyldisiloxane dianhydride represented by the formula:

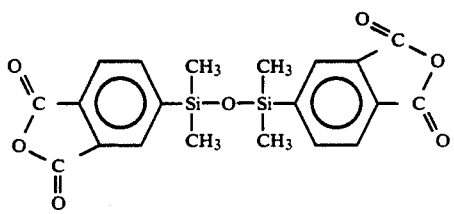

has a melting point of 137° C. to 138° C. and is used as an epoxy resin curing agent to give a cured product excellent in adhesiveness and resistance to moisture. The above-mentioned symmetric compound can be synthesized as disclosed in J. Org. Chem. vol. 38, p 4271 (1973); "Polyimides" ed. by K. L. Mittal, vol. 1, p 1 (1984) published by Plenum Press Co.; and Japanese Patent Unexamined Publication No. 61-83191.

But since said compound has a melting point as high as 137° to 138° C., it is necessary to mix with an epoxy resin with heating. When a curing accelerator is added, there arise problems in that a pot life becomes very short, and gelation easily takes place at the time of mixing.

SUMMARY OF THE INVENTION

It is an object of the present invention to provide a tetracarboxylic acid dianhydride having a disiloxane linkage with a low melting point and excellent in processability to solved the above-mentioned problems. It is another object of the present invention to provide a process for producing said compound.

This invention provides 1-(2,3-dicarboxyphenyl)-3-(3,4-dicarboxyphenyl)-1,1,3,3-tetramethyldisiloxane dianhydride represented by the formula:

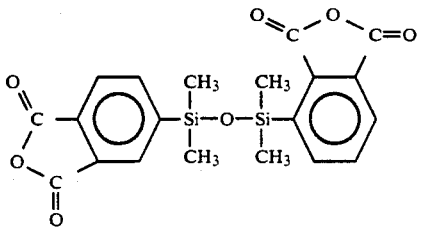

This invention also provides a process for producing the compound of the formula (I), which comprises dispersing a mixture of 1,3-bis(dicarboxyphenyl)-1,1,3,3-tetramethyldisiloxane dianhydrides represented by the formula:

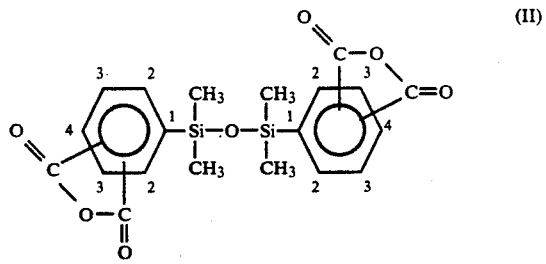

wherein the acid anhydride groups are independently bonded to 2,3-positions or 3,4-positions, in an ether, removing deposited crystals of 1,3-bis(3,4-dicarboxyphenyl)-1,1,3,3-tetramethyldisiloxane dianhydride of the formula:

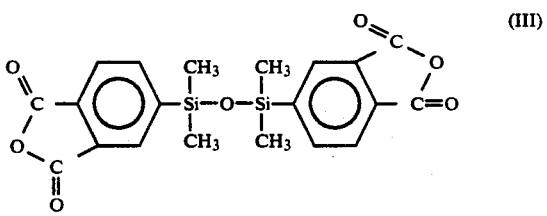

from the ether dispersion, and adding a liquid alkane to the ether dispersion to deposit crystals of the desired compound of the formula (I).

BRIEF DESCRIPTION OF THE DRAWINGS

FIG. 3 is an infrared spectrum of the compound of the formula (I).

DESCRIPTION OF THE PREFERRED EMBODIMENTS

Figure 1:
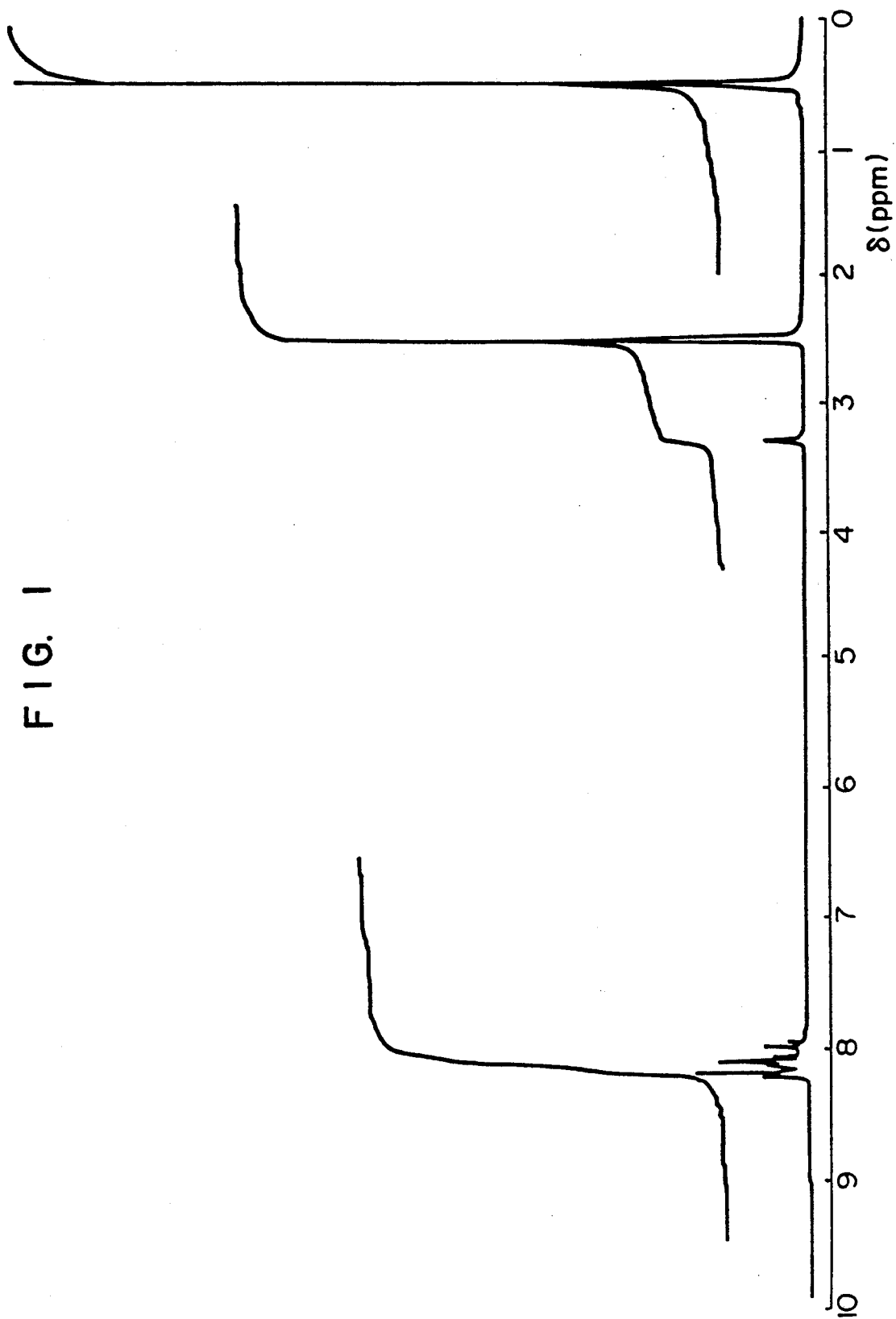
FIG. 1 is $^1$HNMR spectrum of the compound of the formula (I).

The tetracarboxylic dianhydride having a disiloxane linkage is 1-(2,3 dicarboxyphenyl)-3-(3,4-dicarboxyphenyl)-1,1,3,3-tetramethyldisiloxane dianhydride represented by the formula:

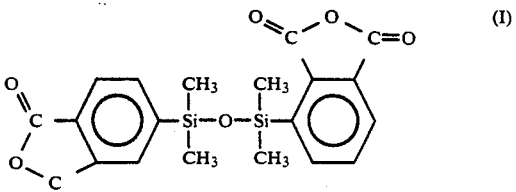

and having a melting point of 118° to 120° C., which is lower than that of 1,3-bis(3,4-dicarboxyphenyl)-1,1,3,3-tetramethyldisiloxane dianhydride by 18° to 19° C. due to its unsymmetric structure.

When the compound of the formula (I) is mixed with 1,3-bis(3,4-dicarboxyphenyl)-1,1,3,3-tetramethyldisiloxane dianhydride of the formula:

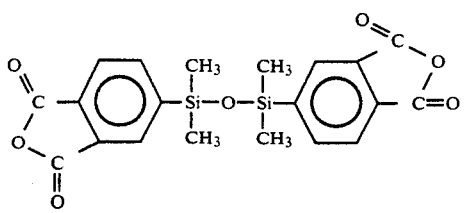

(III)

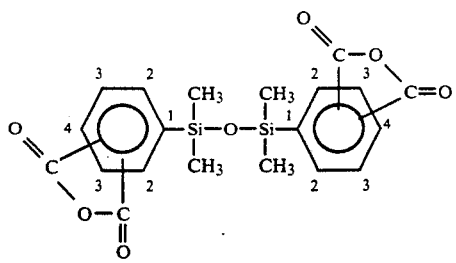

(II)

wherein the acid anhydride groups are independently bonded to 2,3-positions or 3,4-positions, in an ether, removing deposited crystals of the compound of the formula (III) from the ether dispersion, and adding a liquid alkane to the ether dispersion to deposit crystals of the desired compound of the formula (I).

The mixture of the compounds of the formula (II) are known compounds and can be synthesized as follows.

First, a mixture of 4-bromo-o-oxylene and 3-bromo-o-xylene is reacted with metallic magnesium to yield a Grignard reagent.

To this, dimethylchlorosilane is added to carry out a coupling reaction to yield dimethylsilane.

Then, hydroxylation is carried out using a palladium catalyst to yield dimethylphenyldimethylphenyldimethylhydroxysilane, followed by hydrolysis using an acid catalyst to yield 1,3-bis(dimethylphenyl)-1,1,3,3-tetramethyldisiloxane. This compound is oxidized using potassium permanganate to yield 1,3-bis(dicarboxyphenyl- 1,1,3,3-tetramethyldisiloxane, followed by dehydration ring closure with heating to give the mixture of compounds of the formula (II).

The above-mentioned process can be illustrated by the following reaction schema:

the melting point of the resulting mixture is further lowered to give a mixture of acid anhydrides which can melt at lower temperatures. For example, a 1:1 (by weight) mixture of the compounds of the formulae (I) and (III) becomes a viscous liquid immediately after the melt mixing. Thus, an epoxy resin can be mixed with the above-mentioned curing agent mixture at that time. When the above-mentioned mixture is allowed to stand at room temperature for a long period of time, it is gradually crystallized to give a solid having a melting point of 92° to 96° C., which temperature is 40° C. or lower compared with that of the compound of the formula (III).

The compound of the formula (I) is produced by dispersing a mixture of 1,3-bis(dicarboxyphenyl)-1,1,3,3-tetramethyldisiloxane dianhydrides represented by the formula:

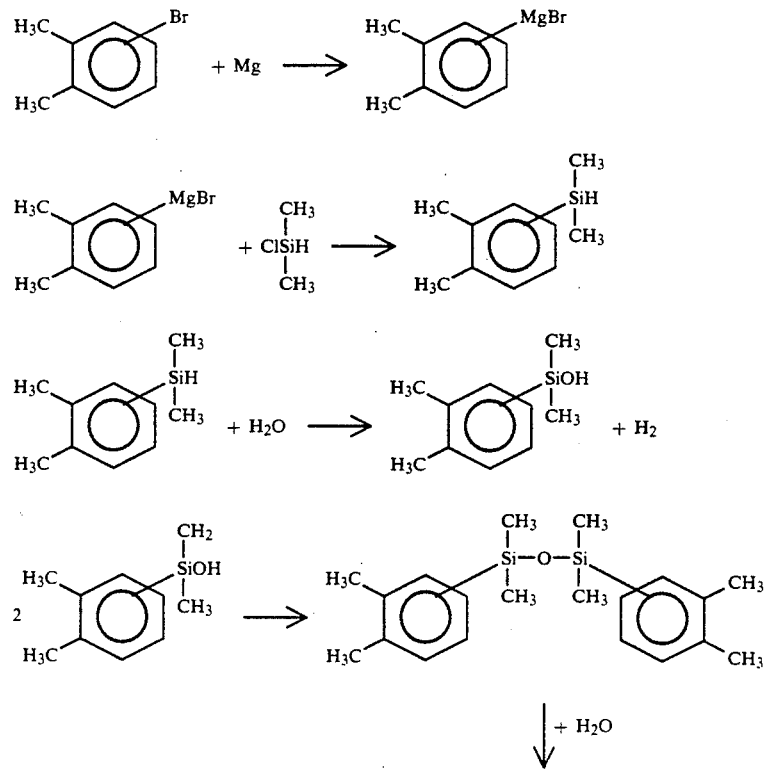

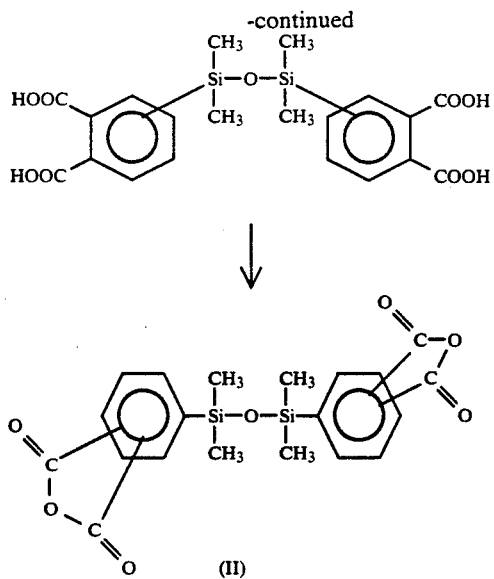

Since the mixture of 4-bromo-o-xylene and 3-bromo-o-xylene is used as a starting material, the resulting acid anhydride includes the desired compound of the formula (I) as well as 1,3-bis(3,4-dicarboxyphenyl)-1,1,3,3-tetramethyldisiloxane dianhydride and 1,3-bis(2,3-dicarboxyphenyl)-1,1,3,3-tetramethyldisiloxane dianhydride.

The thus obtained mixture of acid anhydrides of the formula (I) is a brown viscous liquid and not purified at this stage, so that by-products of the oxidizing reaction are also included therein. Thus, said mixture cannot be used as a curing agent for epoxy resins or a starting material for polyimide resins.

The mixture of the compounds of the formula (II) is then dispersed in an ether to deposit crystals of the compound of the formula (III).

As the ether, there can be used diethyl ether, diisopropyl ether, di-n-propyl ether, etc.

The ether is used in an amount of preferably 100 to 500% by weight based on the weight of compounds of the formula (II). When the amount is less than 100% by weight, the amount of the solvent is too small to disperse well. On the other hand, when the amount is more than 500% by weight, the compound of the formula (III) is undesirably dissolved in the ether.

The dispersion is preferably carried out at a temperature of 10° C. or higher and a reflux temperature or lower of an ether used as a solvent until a resinous material disappears with stirring or reflux.

After cooling gradually, deposited crystals of 1,3-bis(3,4-dicarboxyphenyl)-1,1,3,3-tetramethyldisiloxane dianhydride (compound of the formula (III)) is removed by filtration.

To the resulting filtrate containing the compound of the formula (I) [1-(2,3-dicarboxyphenyl)-3-(3,4-dicarboxyphenyl)-1,1,3,3-tetramethyldisiloxane dianhydride], a liquid alkane as a solvent is added to deposit the desired compound of the formula (I).

As the liquid alkane, there can be used that having preferably having 5 to 15 carbon atoms, such as n-hexane, cyclohexane, n-pentane, n-heptane, 2,2,4-trimethylpentane, etc. The amount of the alkane is preferably 10 to 100% by weight based on the amount of the filtrate. When the amount is less than 10% by weight, the amount of the desired product deposited as crystals is undesirably lowered. On the other hand, when the amount is more than 100% by weight, the using amount of the solvent is increased without increasing the yield of the desired compound.

The thus obtained compound of the formula (I) is in the form of crystals, so that the purity can be improved by recrystallization.

The compound of the formula (I) has an unsymmetrical molecular structure, so that it has a lower melting point compared with the compound of the formula (III). Thus, the compound of the formula (I) is useful as a catalyst for epoxy resins excellent in processability.

The present invention is illustrated by way of the following Examples, in which all percents are by weight unless otherwise specified.

EXAMPLE 1

(1) Synthesis of 1,3-bis(dicarboxyphenyl)-1,1,3,3-tetramethyldisiloxane dianhydride (i) Preparation of Grignard Reagent A 2-liter four-necked flask equipped with an Allihn condenser, a liquefying funnel, a thermometer and a stirrer was sufficiently dried in an argon atmosphere. Then, 100 ml of tetrahydrofuran dehydrated with metallic sodium, 9.72 g of metallic magnesium and 10.0 g of bromo-o-xylene (a mixture of 75% of 4-bromo-o-xylene and 25% of 3-bromo-o-xylene) were added thereto. When the reaction solution began to produce turbidity and a Grignard reagent, a mixture of 64.0 g of the same bromo-o-oxylene as mentioned above and 100 ml of tetrahydrofuran was added thereto in one hour dropwise. During this time, the reaction solution was kept at 40° C. while cooling in an ice bath since the reaction is an exothermic reaction. After the completion of the dropping, since metallic magnesium is retained, the reaction solution was maintained at 40° C. by heating the oil bath for 5 hours with stirring to completely react the metallic magnesium to form the Grignard reagent.

(ii) Coupling Reaction

Then, 37.85 g (0.40 mole) of dimethylchlorosilane was added to the reaction solution from a dropping funnel for 20 minutes. During this time, the reaction temperature was maintained at 20° C. After the completion of the dropping, the reaction solution was kept at 20° C. for 5 hours to complete the coupling reaction.

Then, 100 ml of deionized water was gradually added to the reaction solution to make the chlorobromo magnesium produced in the coupling reaction an aqueous solution. In the flask, the reaction solution was separated into two layers, the upper layer of which is a tetrahydrofuran solution containing dimethylphenyldimethylsilane and the lower layer of which is an aqueous layer. After removing the lower layer, the upper layer was washed with 50 ml of deionized water four times and dried over anhydrous sodium sulfate.

(iii) Hydroxylation Reaction

In a 1-liter flask equipped with an Allihn condenser, a thermometer and a stirrer, the whole amount of tetrahydrofuran solution of dimethylphenyldimethylsilane was placed, followed by addition of 20 ml of deionized water and 0.3 g of a catalyst of 5% palladium carried on activated carbon (0.023% of metallic palladium based on the weight of dimethylphenyldimethylsilane) with stirring at 23° C. to immediately generate hydrogen gas. The generated hydrogen amount was measured by a wet gas meter attached to an outlet of the Allihn condenser. The generation of hydrogen gas was ended after 2.5 hours from the beginning of the reaction. The generated gas amount was 9.57 liters (0.394 mole) at 23° C.

After the reaction, the reaction solution was filtered to remove the palladium catalyst, followed by separation of a lower aqueous layer to give a tetrahydrofuran solution of dimethylphenyldimethylhydroxysilane.

(iv) Hydrolysis

In a 1-liter flask equipped with an Allihn condenser, a thermometer and a stirrer, the whole amount of tetrahydrofuran solution of dimethylphenyldimethylhydroxysilane was placed, followed by addition of 15 ml of 36% hydrochloric acid with stirring at 20° C. to carry out the reaction for 8 hours. After the reaction, a lower aqueous layer of hydrochloric acid was removed by a separatory funnel. Then, 100 ml of toluene was added to the resulting tetrahydrofuran solution of 1,3-bis(dimethylphenyl)-1,1,3,3-tetramethyldisiloxane, followed by washing with 70 ml of deionized water three times. Using an evaporator, the tetrahydrofuran and toluene were removed by distillation to give 66.8 g (0.195 mole) of 1,3 bis(dimethylphenyl)-1,1,3,3-tetramethyldisiloxane.

The obtained compound was analyzed by gel permeation chromatography to give 98% of 1,3-bis(dimethylphenyl)-1,1,3,3-tetramethyldisiloxane, 1.5% of a compound presumably a polysiloxane compound and 0.5% of unreacted hydroxysilane compound.

The obtained product was purified using a distillator equipped with a Vigreaux distillation head to give 62.1 g of a fraction having a boiling point of 141° to 144° C. (under a pressure of 0.52 mmHg). This fraction was identified as 1,3-bis(dimethylphenyl)-1,1,3,3-tetramethyldisiloxane by proton-NMR analysis.

(v) Oxidation

In a 1-liter four-necked flask equipped with an Allihn condenser, a thermometer and a stirrer, 13.7 g (40 mmoles) of 1,3-bis(dimethylphenyl)-1,1,3,3-tetramethyldisiloxane, 240 ml of pyridine and 120 ml of deionized water were placed and heated to 85° C. Subsequently, 75.9 g (480 mmoles) of potassium permanganate was gradually added thereto over 2 hours, and stirring was continued at 85° C. for additional 4 hours. A precipitate of manganese oxide generated by the reaction was removed by filtration, followed by removal of pyridine in the filtrate by distillation using a rotary evaporator and precipitation with 36% hydrochloric acid to give a white resinous precipitate. The pH of the aqueous layer was 1. The precipitate was dissolved in a mixed solvent of 220 ml of tetrahydrofuran and 150 ml of toluene, washed with 75 ml of 10% sodium chloride aqueous solution 4 times, followed by removal of the solvent by distillation using a rotary evaporator to give 17.4 g (37.6 mmoles) of 1,3-bis(dicarboxyphenyl)-1,1,3,3 -tetramethyldisiloxane as a pale yellowish brown resinous material.

(vi) Dehydration Ring Closure Reaction

In a 100-ml egg-plant type flask, 13.9 g (30 mmoles) of the thus obtained 1,3-bis(dicarboxyphenyl)-1,1,3,3-tetramethyldisiloxane was placed and heated at 150° C. for 3 hours under a reduced pressure of 0.7 mmHg to carry out dehydration ring closure. Thus, 12.4 g (29 mmoles) of resinous 1,3-bis(dicarboxyphenyl)-1,1,3,3-tetramethyldisiloxane dianhydride mixture was obtained.

(2) Production of 1-(2,3-dicarboxyphenyl)-3-(3,4-dicarboxyphenyl)-1,1,3,3-tetramethyldisiloxane dianhydride The thus obtained 1,3-bis(dicarboxyphenyl)-1,1,3,3-tetramethyldisiloxane dianhydride mixture as a resinous viscous material in an amount of 10 g was placed in a 100-ml egg-plant type flask equipped with a condensor. Then, 25 ml (17.9 g) of ethyl ether was added thereto, followed by refluxing for 4 hours with heating. After allowing to stand for cooling, 1,3-bis(3,4-dicarboxyphenyl)-1,1,3,3-tetramethyldisiloxane dianhydride deposited as white powdery crystals was removed by filtration. To the resulting filtrate in an amount of 20 g, 5.0 g of n-hexane was gradually added dropwise with stirring at room temperature. Stirring was continued after the addition, and after 10 minutes, fine white crystals were deposited. The crystals were separated by filtration, followed by drying to give 3.4 g of crystals.

The resulting crystals in an amount of 3.0 g was dissolved in 10 ml (7.2 g) of ethyl ether with heating for dissolution, filtered while hot, followed by cooling of the resulting filtrate. Deposited crystals were taken out and dried to yield 2.4 g of crystals.

Elementary analysis of the obtained crystals was as follows:

|  | C(%) | H(%) |
| --- | --- | --- |
| Found | 55.93 | 4.21 |
| Calculated | 56.32 | 4.25 |

The results mean that the found values are very close to the calculated values of 1-(2,3-dicarboxyphenyl)-3-(3,4-dicarboxyphenyl)-1,1,3,3-tetramethyldisiloxane dianhydride.

The crystals had a melting point of 118° to 120° C.

The crystals were subjected to analysis by $^1$H-NMR (using a Hitachi R-250 type nuclear magnetic resonance spectrometer mfd. by Hitachi, Ltd.). The results are shown in FIG. 1. In FIG. 1, the absorption at 2.5 ppm is due to dimethylsulfoxide (DMSO, a solvent), and the absorption at 3.3 ppm is due to water in the solvent. Further, the absorptions at 0.485 ppm and 0.495 ppm are due to the methyl group proton bonded to silicon, but since the molecule is unsymmetrical, the absorption is separated into two. In addition, the absorption at 7.93 to 8.20 ppm is due to benzene ring proton. The integration intensity ratio of the methyl group proton to the benzene ring proton is 182:92 (12:6.07), which value is in good agreement with the theoretical value of 12:6 of 1-(2,3-dicarboxyphenyl)-3-(3,4-dicarboxyphenyl)-1,1,3,3-tetramethyldisiloxane dianhydride.

Figure 2:
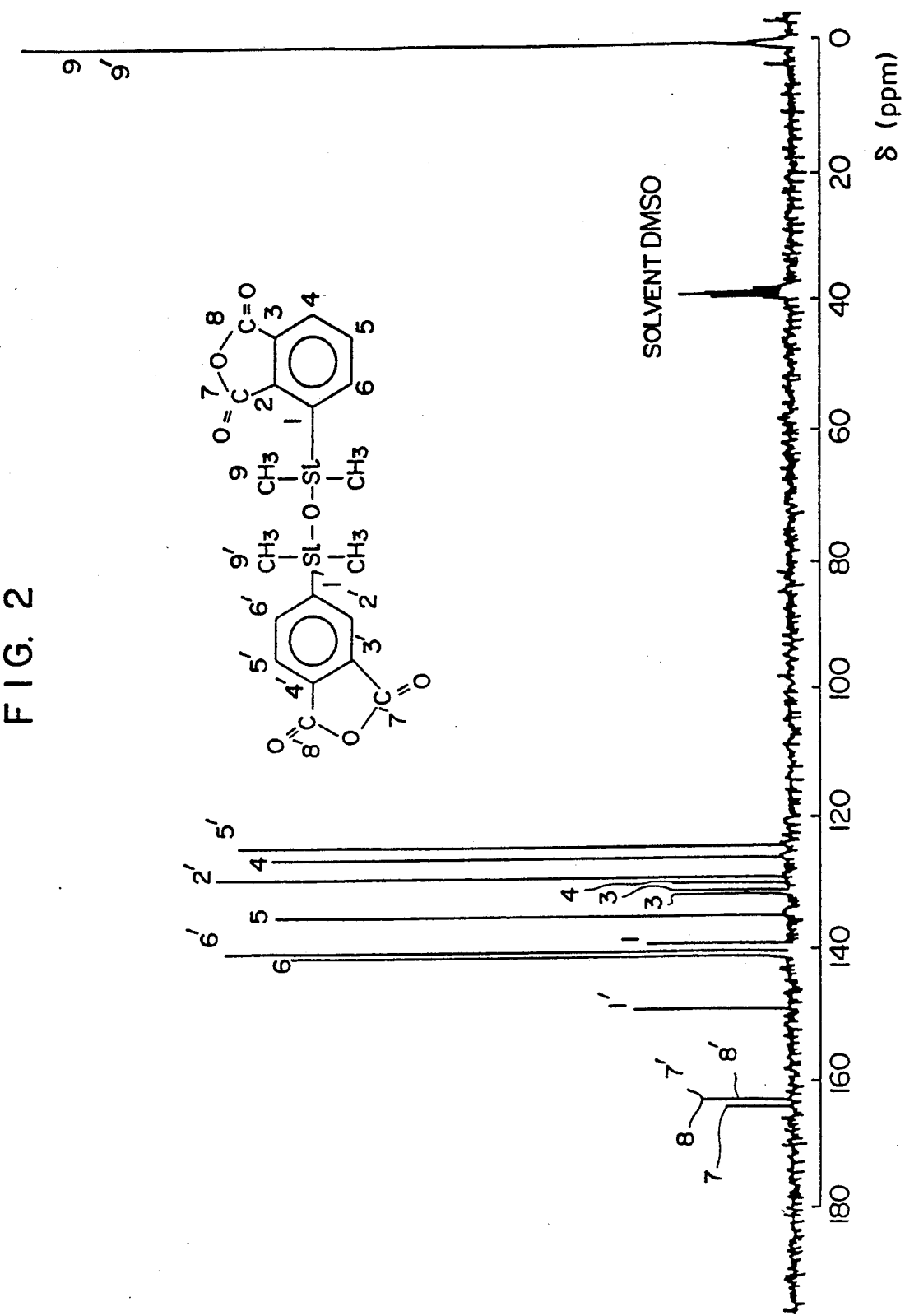
FIG. 2 is $^{13}$C-NMR spectrum of the compound of the formula (I).

The crystals were also subjected to analysis by $^{13}$C-NMR (using a Hitachi R-250 type nuclear magnetic resonance spectrometer mfd. by Hitachi, Ltd.). The results are shown in FIG. 2. As shown in FIG. 2, 18 peaks are shown as expected from the theory. In FIG. 2, the peak of carbon ⑧ and that of carbon ⑦' are overlapped due to very close chemical shift values of 165.793 ppm and 165.762 ppm, respectively, which results in appearing as one line in FIG. 2. The peak of the carbon ⑨ and that of carbon ⑨' are close but separately appear at 3.172 ppm and 3.004 ppm, respectively.

From the above experimental results, it was identified that the obtained crystals are those of 1-(2,3-dicarboxyphenyl)-3-(3,4-dicarboxyphenyl)-1,1,3,3-tetramethyldisiloxane dianhydride.

Infrared absorption spectrum of the crystals was also measured (using a Hitachi 260-30 type infrared spectrophotometer mfd. by Hitachi, Ltd.; KBr method) and shown in FIG. 3. From this, it is also identified that the crystals are those of 1-(2,3-dicarboxyphenyl)-3-(3,4-dicarboxyphenyl)-1,1,3,3-tetramethyldisiloxane dianhydride.

APPLICATION EXAMPLE 1

In a test tube, 1.0 g of 1-(2,3-dicarboxyphenyl)-3-(3,4-dicarboxyphenyl)-1,1,3,3-tetramethyldisiloxane dianhydride obtained in Example 1 and 1.0 g of 1,3-bis(3,4-dicarboxyphenyl)-1,1,3,3-tetramethyldisiloxane dianhydride were placed and melt mixed with heating. To this, 1.8 g of bisphenol A diglycidyl ether type epoxy resin having an epoxy equivalent weight of 190 was added, but the liquid state was maintained at room temperature. This means that mixing with an epoxy resin at room temperature is possible.

APPLICATION EXAMPLE 2 (COMPARISON)

In a test tube, 1.1 g of 1,3-bis(3,4-dicarboxyphenyl)-1,1,3,3-tetramethyldisiloxane dianhydride and 1.0 g of the same epoxy resin as used in Application Example 1 were placed and melt mixed at 140° C. with heating. When the resulting mixture was cooled to room temperature, white crystals of 1,3-bis(3,4-dicarboxyphenyl)-1,1,3,3-tetramethyldisiloxane dianhydride were deposited.

What is claimed is:

1. 1-(2,3-Dicarboxyphenyl)-3-(3,4-dicarboxyphenyl)-1,1,3,3-tetramethyldisiloxane dianhydride.

2. A 1:1 by weight mixture of 1-(2,3-dicarboxyphenyl)-3-(3,4-dicarboxyphenyl)-1,1,3,3-tetramethyldisiloxane dianhydride and 1,3-bis(3,4-dicarboxyphenyl)-1,1,3,3-tetramethylsiloxane dianhydride.

3. An epoxy resin curing agent which consists essentially of 1-(2,3-dicarboxyphenyl)-3-(3,4-dicarboxyphenyl)-1,1,3,3-tetramethyldisiloxane dianhydride.

4. An epoxy resin curing agent consisting essentially of a 1:1 by weight mixture of 1-(2,3-dicarboxyphenyl)-3-(3,4-dicarboxyphenyl)-1,1,3,3-tetramethyldisiloxane dianhydride and 1,3-bis(3,4-dicarboxyphenyl)-1,1,3,3-tetramethylsiloxane dianhydride.

5. An epoxy resin curing agent consisting of 1-(2,3-dicarboxyphenyl)-3-(3,4-dicarboxyphenyl)-1,1,3,3-tetramethyldisiloxane dianhydride.

6. An epoxy resin curing agent consisting of a 1:1 by weight mixture of 1-(2,3-dicarboxyphenyl)-3-(3,4-dicarboxyphenyl)-1,1,3,3-tetramethyldisiloxane dianhydride and 1,3-bis-(3,4-dicarboxyphenyl)-1,1,3,3-tetramethylsiloxane dianhydride.

* * * * *